(12) United States Patent
Schellhas

(10) Patent No.: US 6,375,325 B1
(45) Date of Patent: Apr. 23, 2002

(54) PORTABLE DIGITAL VERTICAL PUPIL METER

(76) Inventor: Eric German Schellhas, Ocampo 370, 2000 Rosario (AR)

( * ) Notice: Subject to any disclaimer, the term of this patent is extended or adjusted under 35 U.S.C. 154(b) by 0 days.

(21) Appl. No.: 09/557,851

(22) Filed: Apr. 26, 2000

(30) Foreign Application Priority Data

Apr. 26, 1999 (AR) ..................................... P99 01 01913

(51) Int. Cl.[7] .............................................. A61B 3/00
(52) U.S. Cl. ..................................................... 351/204
(58) Field of Search ................................. 351/200, 204, 351/205, 206, 208, 210, 246, 41, 221; 600/558

(56) References Cited

U.S. PATENT DOCUMENTS

| 5,592,248 A | * | 1/1997 | Norton et al. | 351/246 |
| 6,022,109 A | * | 2/2000 | Dal Santo | 351/221 |
| 6,116,736 A | * | 9/2000 | Stark et al. | 351/206 |

* cited by examiner

Primary Examiner—George Manuel
(74) Attorney, Agent, or Firm—Lyon & Lyon LLP

(57) ABSTRACT

A portable digital vertical pupil meter of the type used to measure the distance between any part of the human eye or eyelid and any point of the periphery of the frame of the glasses. An elongated case is divided into two separable parts, in one of which it has a first opening in its top end provided with a transparent window capable of determining a reference signal. The one part being also provided in the same area with two holes, being provided in its interior with a trigger which is linked to the inferior extreme of a lever, which part has in the other end a pin in each of the holes. The other part of the case has in its top end a second opening similar and opposed to the first one, which opening is also provided with a transparent window that is also capable of determining a reference signal at a point of its height. Under this second there is a means of traction and thrust that is externally operable and linked to the inferior end of an arm, and the top end of this arm has a reference signal virtually visible from the outside of the case, which reference signal is capable of being projected at a height. The inner part of the case has an area in which there is an electric source which activates an electronic circuit and a light source used in aligning the meter with the eye.

20 Claims, 4 Drawing Sheets

PORTABLE DIGITAL VERTICAL PUPIL METER

The present invention is directed to a device for properly fitting the lenses of eyeglasses to the eyes of a patient and, in particular, to a portable digital vertical pupil meter which is especially built to measure the distance between the pupil or the eyelid of the human eye and the base of the frame of the eyeglasses worn by the patient, but it also can be used to measure the distance between any part of the human eye and the base of the frame.

The pupil meter of this invention is mainly constituted by a digital ruler, which is operatively linked to a horizontal reticle provided with a vertically movable implement, all of which is assembled in a light case of small dimensions, which is handled manually by the user. Preferably, the case is formed by two separable parts.

This digital ruler preferably is provided with a sensor that consists of a resistance and a lever that, when moved, and through a microprocessor, determines the distances that will be conveyed to a transmitter of infrared rays, which is operatively linked to an information receiver, although this is not absolutely necessary, since the meter can also operate for only a digital reading when there is no need to transmit or store information.

Inside the case, there is an operable device with two pins whose free ends can extend out of the case and press against a self-adhesive sticker which, due to this pressure, will be fixed on the lenses, test lenses or the like.

The case of this pupil meter preferably is also provided with at least one light that will activate the pupilar reflex as well as with an eye selector that will specify the operational area on the right or left eye, with the pupil meter being able to memorize the information through a control.

This pupil meter works on a source of energy, such as a battery, that operates an electric circuit.

For this device to be clearly understood and easily put into practice, it has been described in one of its preferred forms of realization and shown in the drawings attached to this description, which drawings are presented for the sake of illustration and not of restriction, as follows.

Figure 1:
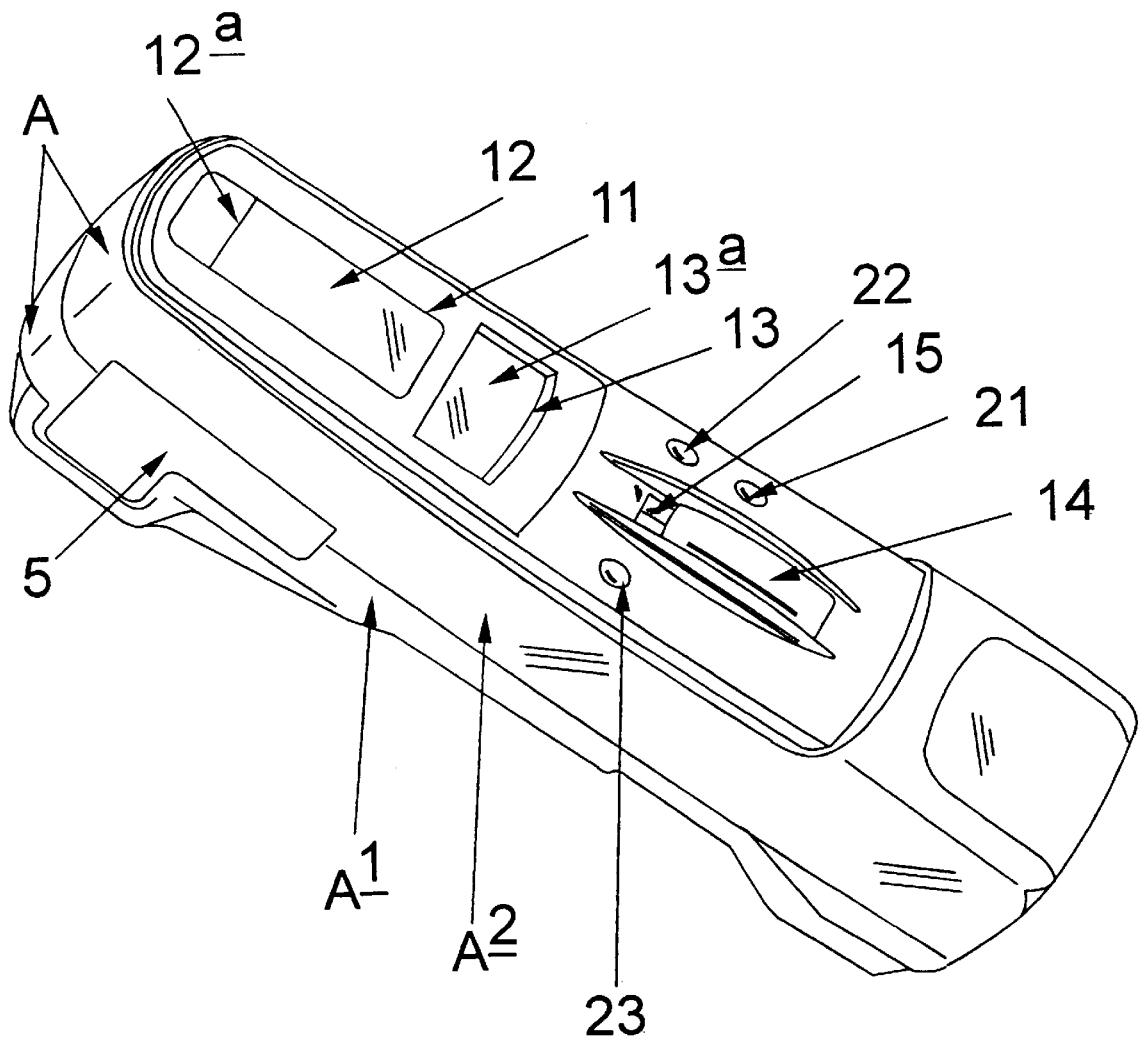
FIG. 1 is a perspective front view of the device of this invention.
Figure 2:
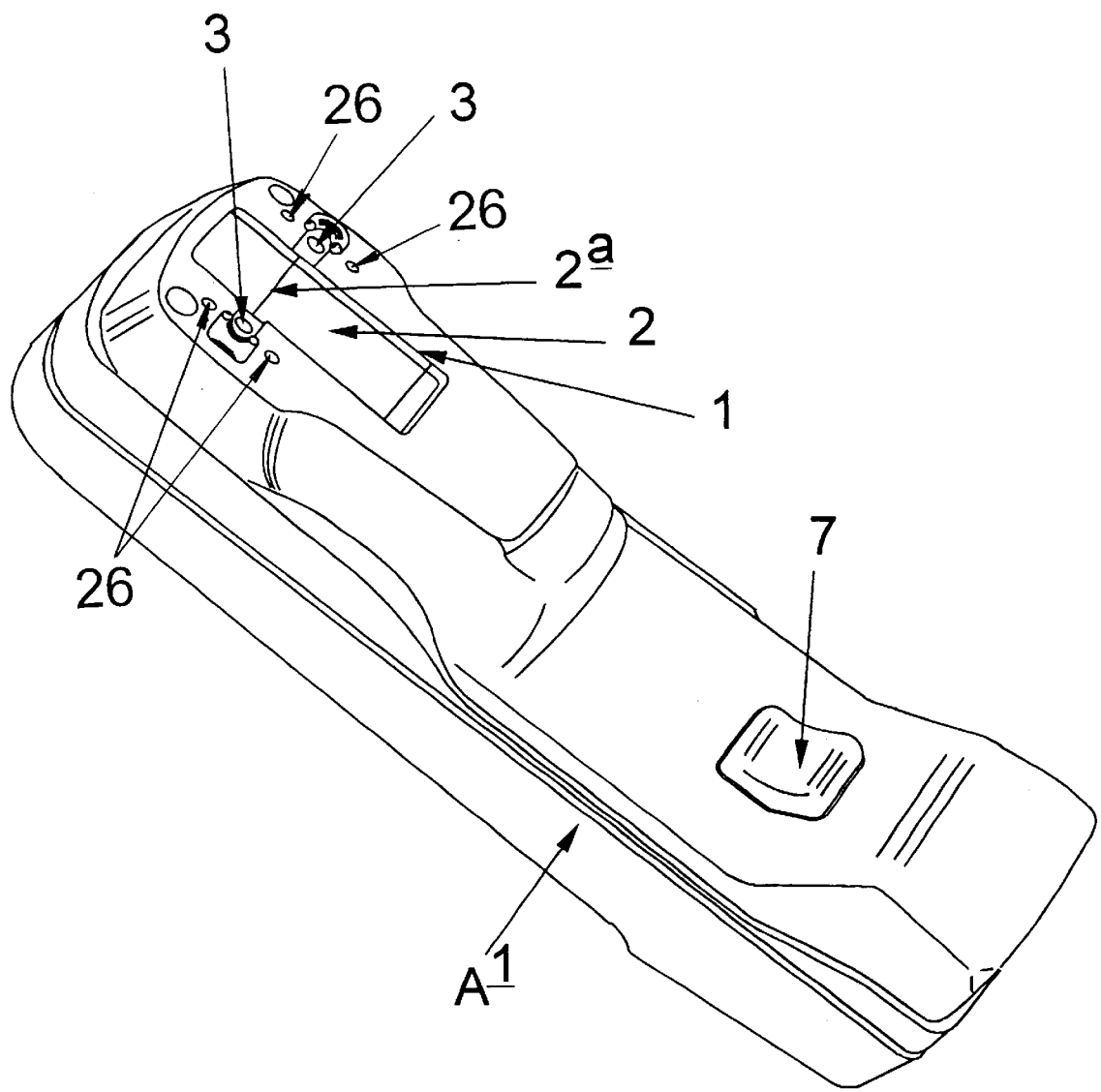
FIG. 2 is a perspective rear view of the device.
Figure 3:
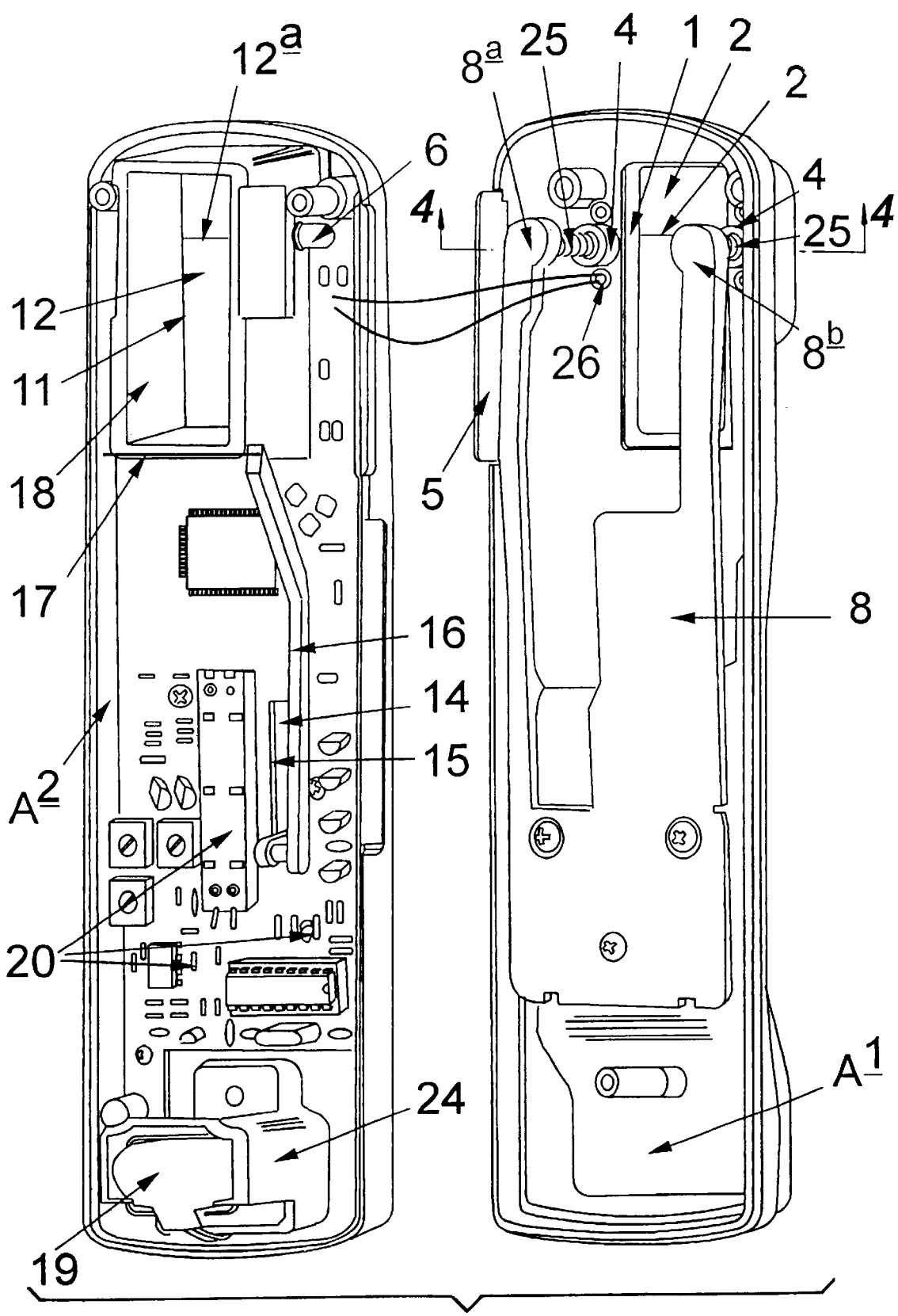
FIG. 3 shows the device with its two separate parts opened to expose the inside in which the components that make up the device are seen.
Figure 4:
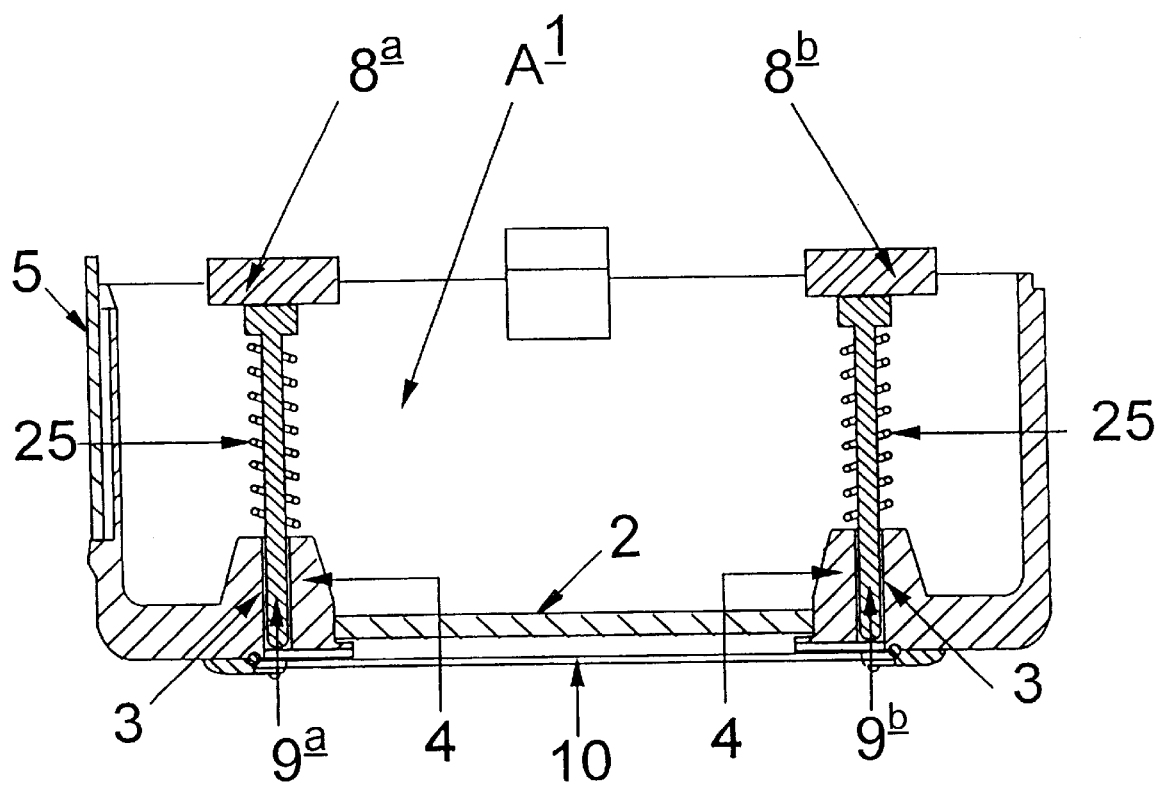
FIG. 4 is a sectional view taken on the line 4—4 in FIG. 3.

Referring now to all the Figures, the corresponding parts of the pupil meter are shown with the same numbers and letters. The pupil meter is essentially constituted by a case A divided into two parts A1 and A2, with part A1 presenting a first opening 1 at its top end, preferably of a quadrangular configuration, vertically set and provided with a transparent window 2 which at a certain point of its height shows a fixed horizontal line that intersects and coincides with the respective centers of two holes 3. Each hole 3 is provided in a projection 4 (see FIGS. 3 and 4) situated inside part A1.

On one side of part A1 and aligned with opening 1, there is a translucent window 5, through which an infrared transmitter 6, which, like a television remote control, allows, if wished, transmitting the information through a receptive means to a means such as a computer or printer (not shown). Part A1 is provided with a tip ejector trigger 7, through which a lever 8 operates on one of its ends while its remaining end fingers 8a and 8b are provided adjacent to two slide pins 9a and 9b in the holes 3 so that when the lever 8 is pressed from outside, by the tip ejector trigger 7, the end fingers 8a and 8b of the lever 8, provided with the pins 9a and 9b are caused to extend out of the holes 3 and to engage and to stick on the eye glass lens that is being checked by each of the tips engaging a self adhesive sticker 10 (FIG. 4), which is set in front of the holes 3.

Each of those pins 9a and 9b is provided with a compression spring 25 set between the free end of each of the projections 4 and a head on each pin that engages the lower surface of the free end fingers 8a and 8b of the lever 8 so that when the trigger 7 is pressed and makes the free end of the lever 8 move down, it causes the springs to compress for allowing the pins 9a and 9b to slide inside the holes 3, but when the pressure against the trigger 7 is released, the springs 25 cause the pins to recede to their rest position.

The outer surface of part A2 of case A presents at its top a second opening 11 similar to the first opening 1 in part A1, which opening 11 is aligned with opening 1 when case A is assembled. This second opening 11 is provided with a transparent window 12, in which aligned with the horizontal line 2a there is another horizontal line 12a, that is also fixed but set slightly above and parallel to line 2a.

Under this second opening 11 there is another opening or area 13 closed at the front by a transparent plate 13a which contains a Liquid Crystal Display (LCD) through which the measurement data, such as the pupilar or eyelid distance or height to the base of the frame of the eyeglasses can be read.

Under this second opening 11 and area 13 there is a means for traction and thrust, such as a thumb switch 14, sliding in a slide bar opening 15, and linked to this means of traction and thrust is a vertically extending arm 16 which at its free end has a needle 17 set horizontally and parallel to the horizontal lines 2a and 12a This needle slides on the open border of a box 18 which projects from the internal surface of part A2 and is set concentrically to the second opening 11.

In the inner bottom section of A2 there is an area 24 inside which there is an electric source 19, such as a battery, that feeds an electric circuit 20, activated through a trigger switch 21 which makes the vertical pupil meter work. At least one Light Emitting Diode (LED) 26 and preferably four LEDs 26 are provided on part A1 spaced above and below the holes 3, which LED also are activated by the switch 21.

A touch switch 22 is an eye selector through which the right or left eye is selected to store the obtained measurements.

A touch switch 23 stores the obtained measurements or if this touch switch 23 is pressed for a few seconds, it transmits the information through the infrared transmitter 6.

The normal use of the pupil meter of this invention will now be described. An eyeglass frame chosen by the patient is fitted to the patient in a comfortable position and the patient looks through the lenses in a normal, straight-ahead manner. A self-adhesive sticker 10 is applied to the pupil meter across the window 2 with portions over the holes 3. The sticker 10 is transparent, has adhesive on both sides, and preferably also has a line (not shown) extending between the tow holes 3 that coincides with line 21, when the sticker is installed. The pupil meter then is positioned in front of one lens (right or left) of the eye glasses and switch 21 is actuated to activate the LEDs 26. The four reflections from the patient's eye cornea produced by the four LEDs 26 are observed through windows 2 and 12 to thereby align the centering lines 2a and 12a by tilting the pupil meter to make lines 2a and 12a appear as a single line. The single line is preferably centered on the eye pupil but may be aligned with other portions of the eye or eyelid for other purposes, such as for fitting bifocal lenses. The pupil meter is gentle pressed against the eyeglass lenses and then the tip ejector trigger 7 is actuated for causing the adhesive sticker to adhere to the lens by projecting the pins 9, whereupon the pupil is fixed in a position on the lens by the double-sided adhesive sticker 10. Then the thumb switch 14 is moved until the needle 17 is aligned with the frame of the eyeglasses and the circuit 20 calculates the vertical distance between needle 17 and the aligned lines 2a and 12a, which distance is displayed on the LCD in area 13 and can be stored in a memory and/or transmitted by infrared transmitter 6. That distance may then be used for actuately grinding lenses for that eyeglass frame to match the location of the patient's eyes. When the pupil meter is retracted from the eyeglass lens, the sticker 10 remains on the lens and may also be used for making height measurements on the frame. Preferably, the procedure is conducted for both eyes without moving the frame on the patient and the separate dimensions are identified by using touch switch 22.

The claimed invention is:

1. A portable digital vertical pupil meter used to measure a distance between any part of a human eye or eyelid and any point of the periphery of a frame of the eyeglasses comprising an elongated case divided into separable parts, a first part having a first opening in a top end provided with a transparent window capable of determining a first reference signal, said first part being also provided in the same area as said first window with two holes, said first part being provided in its interior with a trigger which is linked to the inferior extreme of a lever, which lever has in the other end two pins in the holes; a second part of the case having a top end with a second opening similar and opposed to the first opening, said second opening also provided with a transparent window that is also capable of determining a second reference signal at a point of its height, under said second opening there is provided an area, under which there is a means of traction and thrust externally operable, linked to a lower inferior end of an arm, a top end of the arm having a third reference signal virtually visible from the outside of the case, this third reference signal capable of being projected at a height; and an inner part of the case having an area in which there is an electric source which activates an electronic circuit for measuring the height.

2. The portable digital vertical pupil meter according to claim 1 wherein the case is provided into only two parts.

3. The portable digital vertical pupil meter according to claim 1, further provided with at least one means of infrared emission.

4. The portable digital vertical pupil meter according to claim 1, wherein an external part of the case has two projections which can come in contact with a sticker provided with a reference signal, which sticker sticks to any material used for frames of glasses.

5. The portable digital vertical pupil meter according to claim 1, wherein the reference signals are essentially constituted by horizontal lines.

6. The portable digital vertical pupil meter according to claim 1 wherein the meter is provided with a variety of reference signals.

7. The portable digital vertical pupil meter according to claim 1, wherein the meter is provided with an eye selector.

8. The portable digital vertical pupil meter according to claim 1, wherein the meter is provided with a data storing device.

9. A portable digital vertical pupil meter for measuring a distance between a part of the human eye or eyelid and a portion of eyeglasses positioned over the human eye, comprising, a case having first and second spaced transparent windows with said first window having a reference indicia for visually aligning with a reference indicia of said second window and relative to the human eye or eyelid, a movable reference indicia mounted in said case for selective movement to a position over the portion of the eyeglasses and visible through said windows, and means for measuring the distance between the position of the movable reference indicia and the aligned said reference indicia of said first and second windows.

10. The portable digital vertical pupil meter according to claim 9, further including a light means in said case facing the human eye for observing a reflection from the human eye for aligning in said reference indicia of said first and second windows relative to said reflection.

11. The portable digital vertical pupil meter according to claim 10, wherein said light means comprises four light sources spaced around one said reference on one said window.

12. The portable digital vertical pupil meter according to claim 9, wherein said means for measuring includes an electrical circuit that measures the distance the movable reference indicia has moved from a position aligned with said reference indicia on said first and second windows.

13. The portable digital vertical pupil meter according to claim 12, wherein said electrical circuit includes means for transmitting a signal corresponding to said measured distance.

14. The portable digital vertical pupil meter according to claim 13, wherein said transmitting means includes an infrared light emitting means.

15. The portable digital vertical pupil meter according to claim 9, further including a self-adhesive sticker for positioning on said case at a predetermined location relative to said reference indicia on one of said windows, and means for selectively applying said sticker to the eyeglasses when reference indicia are aligned.

16. The portable digital vertical pupil meter according to claim 15, wherein said sticker is self adhesive on both sides for temporarily fixing the pupil meter to the eyeglasses.

17. The portable digital vertical pupil meter according to claim 15, wherein said sticker includes a reference indicia for aligning with said reference indicia on said one of said windows.

18. The portable digital vertical pupil meter according to claim 15, wherein said applying means includes a lever with a switch at one end for manually moving the lever, and a pair of pins movably mounted in the case opposite another end of said lever for being moved by said lever, said pins engaging one side of the sticker to move the sticker toward the eyeglasses.

19. The portable digital vertical pupil meter according to claim 15, further including a light means in said case facing the human eye for observing a reflection from the human eye for aligning said reference indicia of said first and second windows relative to said reflection.

20. The portable digital vertical pupil meter according to claim 18, wherein said means for measuring includes an electrical circuit that measures the distance the movable reference indicia has moved from a position aligned with said reference indicia on said first and second windows.

\* \* \* \* \*